United States Patent [19]

Takagawa

[11] Patent Number: 5,371,293
[45] Date of Patent: Dec. 6, 1994

[54] PROCESS FOR PRODUCING BISAMINOMETHYLCYCLOHEXANE

[75] Inventor: Makoto Takagawa, Tsukuba, Japan

[73] Assignee: Mitsubishi Gas Chemical Company, Inc., Tokyo, Japan

[21] Appl. No.: 218,456

[22] Filed: Mar. 28, 1994

Related U.S. Application Data

[63] Continuation of Ser. No. 864,015, Oct. 21, 1992, abandoned.

[30] Foreign Application Priority Data

Oct. 23, 1991 [JP] Japan ................. 3-304103

[51] Int. Cl.$^5$ ............................. C07C 209/48
[52] U.S. Cl. ........................ 564/449; 564/455
[58] Field of Search ................... 564/449, 455

[56] References Cited

U.S. PATENT DOCUMENTS

| | | | |
|---|---|---|---|
| 3,177,258 | 4/1965 | Rylander et al. | 564/449 |
| 3,998,881 | 12/1976 | Butte, Jr. et al. | 564/449 |
| 4,070,399 | 1/1978 | Butte, Jr. | 564/449 |
| 4,181,680 | 1/1980 | Butte, Jr. et al. | 564/451 |
| 4,222,961 | 9/1980 | Butte, Jr. et al. | 564/449 |

FOREIGN PATENT DOCUMENTS

| | | |
|---|---|---|
| 1305090 | 8/1962 | France . |
| 48-32845 | 5/1973 | Japan . |
| 50-126638 | 10/1975 | Japan . |
| 51-7659 | 3/1976 | Japan . |
| 54-41804 | 3/1979 | Japan . |
| 54-16452 | 7/1979 | Japan . |
| 56-63944 | 5/1981 | Japan . |

OTHER PUBLICATIONS

*Chemical Abstracts*, vol. 78, No. 6, Feb. 12, 1973, page 2, No. 30232h, Zhubonov et al., "Polyamides based on 1,4–bis(aminomethyl)cyclohexane."

*Primary Examiner*—Glennon H. Hollrah
*Assistant Examiner*—Scott C. Rand
*Attorney, Agent, or Firm*—Armstrong, Westerman, Hattori, McLeland & Naughton

[57] ABSTRACT

Bisaminomethylcyclohexane is produced in high yield by one-stage process from an aromatic dinitrile by hydrogenating the aromatic dinitrile in the presence of a ruthenium catalyst containing 1 to 10% by weight of ruthenium, in terms of metallic ruthenium, supported on a carrier, and in the presence of 0.5 parts by weight or more of liquid ammonia per part by weight of the aromatic nitrile at a temperature of 70° to 150° C. and a hydrogen partial pressure of 50 to 150 atm.

2 Claims, No Drawings

PROCESS FOR PRODUCING BISAMINOMETHYLCYCLOHEXANE

This application is a continuation of application Ser. No. 07/964,015 filed Oct. 21, 1992, now abandoned.

BACKGROUND OF THE INVENTION

1. Field of the Invention

The present invention relates to a process for producing bisaminomethyicyclohexane as a useful raw material for polyamide resin and epoxy resin.

It is known that polyamides prepared from bisaminomethylcyclohexane (which will be hereinafter referred to as BAC) and an organic dibasic acid such as adipic acid or sebacic acid are materials having various distinguished properties. It is also known that polyurethane prepared from BAC as a raw material is elastic fibers, moldings or films having a very distinguished light resistance, and recently it has been regarded particularly as a hardening material for epoxy resin.

2. Prior Art

BAC has three isomers, i.e. 1,2-isomer, 1,3-isomer and 1,4-isomer, depending on the location of the aminomethyl groups. Heretofore, BAC has been commercially produced by hydrogenating the nitrile group of an aromatic dinitrile such as phthalonitrile, isophthalonitrile or terephthalonitrile, thereby forming a xylylenediamine, and then hydrogenating the xylylenediamine, thereby forming the corresponding BAC.

In the production of xylylenediamine by hydrogenation of an aromatic dinitrile, a Raney type catalyst such as Raney nickel or Raney cobalt, or a stabilized nickel catalyst, or such a catalyst as a platinum or rhodium catalyst is used, and various attempts have been so far made to increase the yield and the catalyst life. For Example, Japanese Patent Application Kokai (Laid-open) No. 54-41804 discloses hydrogenation reaction in a solvent mixture of a lower alcohol and a cyclic hydrocarbon with a Raney nickel to prevent formation of secondary and tertiary amines. Japanese Patent Application Kokai (Laid-open) No. 56-63944 discloses hydrogenation of an aromatic nitrile in the presence of carbon dioxide with a palladium catalyst.

In the hydrogenation of xylylenediamine, various catalysts have been so far used. For example, Japanese Patent Application Kokai (Laid-open) No. 48-32845 discloses the use of a modified reduced cobalt catalyst and Japanese Patent Application Kokai (Laid-open) No. 50-126638 discloses the use of a ruthenium catalyst supported on an inert inorganic material. In order to increase the yield of BAC in the hydrogenation of xylylenedianine, Japanese Patent Publication No. 51-7659 discloses the use of liquid ammonia as a reaction solvent, and Japanese Patent Application Kokai (Laid-open) No. 54-16452 and U.S. Pat. No. 4,181,680 disclose the use of water as a solvent.

In the above-mentioned two-stage production of BAC, which comprises a first reaction stage of producing xylylenediamine from an aromatic dinitrile and a second reaction stage of hydrogenating the xylylenediamine to produce BAC, a reactor and steps for separating and purifying the reaction product are required for each reaction stage, and thus the one-stage direct production of BAC from the aromatic dinitrile, which combines these two-stage reactions, has been desired owing to its very high commercial significance. In this connection, U.S. Pat. No. 3,998,881 discloses the use of a solvent mixture of a specific organic compound and liquid ammonia with supported rhodium metal as a catalyst and U.S. Pat. No. 4,070,399 discloses the use of a catalyst of both ruthenium and palladium supported on an oxide carrier.

The one-stage direct production of BAC by simultaneous hydrogenation of the nitrile groups and the aromatic nucleus of a corresponding aromatic dinitrile is very advantageous, but its commercial process has not been established. That is, the rhodium used as a catalyst in U.S. Pat. No. 3,998,881 is a very expensive metal, which is not so resourceful. In the catalyst of both ruthenium and palladium supported on the oxide carrier for use in the one-stage production of 1,4-BAC from terephthalonitrile disclosed in U.S. Pat. No. 4,070,399, expensive palladium is used, and deterioration of the catalyst is considerable.

The difficulty of producing BAC from a corresponding aromatic dinitrile in one stage is due to the fact that the effective catalyst for producing an aromatic diamine from an aromatic dinitrile is not always effective for hydrogenating the aromatic nucleus of the aromatic diamine.

SUMMARY OF THE INVENTION

As a result of extensive studies on processes for producing BAC by simultaneous hydrogenation of the nitrile groups and the aromatic nucleus of a corresponding aromatic dinitrile in a commercially advantageous manner, the present inventors have found that BAC can be produced in high yield in one stage by hydrogenation of a corresponding aromatic dinitrile in the presence of ruthenium supported on a carrier as a catalyst and in the presence of ammonia, and have established the present invention.

An object of the present invention is to provide a process for producing bisaminomethylcyclohexane, which comprises hydrogenating an aromatic dinitrile in the presence of a ruthenium catalyst containing 1 to 10% by weight of ruthenium, in terms of metallic ruthenium, supported on a carrier, and in the presence of 0.5 parts by weight or more of liquid anlmonia per part by weight of the aromatic dinitrile at a temperature of 70° to 150° C. and a hydrogen partial pressure of 50 to 150 atm.

The ruthenium catalyst in an effective catalyst for hydrogenation of the aromatic nucleus of an aromatic diamine, but is catalytically too active when used in the hydrogenation of the aromatic dinitrile, causing considerable side reactions such as decomposition, etc. Thus, the ruthenium catalyst has been so far regarded as riot effective for both reactions, i.e. hydrogenation of the nitrile groups of the aromatic dinitrile and hydrogenation of the aromatic nucleus thereof.

The present invention is based on such a finding that both reactions can be made to proceed at the same time by properly selecting reaction conditions in the presence of a specific quantity of the ruthenium catalyst and in the presence of a specific quantity of liquid ammonia in the reaction system, whereby BAC can be produced in high yield.

DETAILED DESCRIPTION OF THE INVENTION

Aromatic dinitriles as raw materials of the present invention are aromatic compounds having two nitrile groups on one benzene nucleus, including three isomers, i.e. phthalonitrile, isophthalonitrile and terephthalonitrile, depending on the positions of the nitrile groups. In the present invention, 1,2-BAC, 1,3-BAC and 1,4-BAC can be obtained, corresponding to the positions of the nitrile groups, by hydrogenating the nitrile groups and the benzene nucleus.

Carriers for the ruthenium include oxide carriers such as alumina, silica, silica-alumina, titania, girconia, etc., and activated carbon.

The quantity of ruthenium supported on the carrier is 1 to 10% by weight, preferably 2 to 8% by weight, in terms of metallic ruthenium. Below 1% by weight of ruthenium, there is a high possibility that the reactions proceed not sufficiently and proportions of side reaction products such as BACs whose one methylamino group is replaced with a methyl group, BACs whose aromatic nuclei are not hydrogenated, and BACs whose substituents are liberated, are increased. Above 10% by weight of ruthenium, no better yield is obtained, and the catalyst cost is increased. This is not economically advantageous.

Ruthenium for the catalyst is metallic ruthenium or ruthenium compounds. Ruthenium compounds are not specifically limited, but must be reduced or oxidized to metallic ruthenium before the reactions.

In the present invention, ammonia must be present in the reaction system. Liquid ammonia is used, and aqueous ammonia is not preferable. The quantity of liquid ammonia is 0.5 parts by weight, or more, preferably 1 to 10 parts by weight, on the basis of one part by weight of an aromatic dinitrile as the raw material. Below 0.5 parts by weight of liquid ammonia, occurrence of side reactions, such as liberation of substituents and secondary amination is considerable, resulting in much production of low boiling and high boiling products. Even above 10 parts by weight of liquid ammonia, no remarkable effect can be obtained on the reactions. This is processwise not advantageous.

In the present invention, the so-called solvent is not particularly required. However, since the raw material aromatic dinitrile is a solid at room temperature, a solvent can be employed to facilitate reaction procedures. In that case, an organic solvent such as dioxane, tetrahydrofuran, etc. are suitably employed to thoroughly dissolve the raw material aromatic dinitrile. Furthermore, alkylbenzenes such as cumene, etc. can be used as a solvent, because of higher solubility of the raw material aromatic dinitrile therein under the reaction conditions.

The reactions proceed in a mixed phase of solid phase (catalyst)-liquid phase (reactants and products, and solvent)-gaseous phase (hydrogen).

In the present invention, the reaction temperature is 70° to 150° C. Below 70° C., the reaction rate will be considerably low, whereas above 150° C. no considerable effect will be obtained on the reaction rate, and rather there is a high possibility of side reactions such as liberation of substituents, polymerization, etc. and of formation of low boiling and high boiling products.

Hydrogen partial pressure for the hydrogenation is 50 to 150 atm. Below 50 atm, the reactions proceed not sufficiently, producing more products of insufficient hydrogenation. The higher the hydrogen partial pressure, the more preferable for the reactions. That is, a hydrogen partial pressure up to 100 atm has a very good effect on the reactions, but above 100 atm the effect is not so remarkable. In view of the economy of the reactor, the hydrogen partial pressure above 150 atm is no more effective.

The reactions can be carried out either batch wise or by one-path flow. A preferable reaction type for the commercial practice is a trickle-bed-type, one-path flow.

PREFERRED EMBODIMENTS OF THE INVENTION

The present invention will be described in detail below, referring to Examples, which are not limitative of the present invention. In Examples and comparative Examples, yield is % by mole of the respective products per raw material aromatic nitrile.

EXAMPLE 1

5 g of alumina powder containing 5% by weight of ruthenium, 26.8 g of isopthalonitrile and 30 g of liquid ammonia were charged into an autoclave having a net capacity of 200 cc, provided with an electromagnetic stirrer, and subjected to reaction at a reaction temperature of 140° C. and a reaction pressure of 150 kg/cm$^2$ for 60 minutes by continuously supplying hydrogen to the autoclave. As a result of analysis of the reaction product liquid, it was found that the yield of 1,3-BAC was 87.8% and 3-methylbenzylamine and metaxylylenediamine were obtained as by-products in yields of 4.8% and 3%, respectively, while the yield of other lower boiling and higher boiling products than the boiling point of the BAC was 4.4%.

EXAMPLE 2

In place of 26.8 g of isophthalonitrile and 30 g of ammonia in Example 1, 24.6 g of terephthalonitrile, 52 g of dioxane and 25 g of ammonia were changed into the same autocLave and subjected to reaction in the same manner as in Example 1. It was found that the yield of 1,4-BAC was 88.2%, the yields of 4-methylbenzylamine and paraxylylenediamine were 7.2% and 2.1%, respectively, and that of other lower boiling and higher boiling products was 2.5%.

EXAMPLE 3

Reaction was carried out in the same manner as in Example 1 except that the reaction temperature was changed to 100° C., the reaction time to 120 minutes, and the carrier to activated carbon. It was found that the yield of 1.3-BAC was 88.3%, the yields of 3-methylbenzylamine, metaxylylenediamine and 1-aminomethyl-3-cyanobenzene as by-products were 2.6%, 3.8% and 1.9%, respectively, and that of other lower boiling and higher boiling products was 3.4%.

Comparative Example 1

Reaction was carried out in the same manner as in Example 1, except that 50 g of dioxane was used in place of 30 g of ammonia. It was found that the yield of 1,3-BAC was 29%, and a large amount of lower boiling compounds without amino group, methylamino group and cyano group was formed.

EXAMPLE 4

650 g of spherical alumina catalysts, 2 mm in diameter, containing 2% by weight of ruthenium, was filled in a vertical reactor tube, 20 mm in inner diameter and 1,500 mm high, and activated with hydrogen at 160° C. 14 g/hr of isophthalonitrile, 140 g/hr of dioxane and 35 g/hr of liquid ammonia were fed to the reactor tube at the top, and 22 l/hr of hydrogen thereto at the bottom to conduct reaction at 130° C. and 110 kg/cm$^2$. After the reaction was brought into the steady state, the reaction product liquid withdrawn at the bottom of the reactor tube was sampled and analyzed. It was found that the yield of 1,3-BAC was 88.4%, that of 3-methylbenzylamine 6.8%, that of 1-aminomethyl-3-methylcyclohexane 1.2%, that of 1-aminomethyl-3-cyanocyclohexane 0.8% and that of metaxylylenediamine 1.6%, and that of other lower boiling and higher boiling products 1.2%.

Comparative Example 2

Reaction was carried out in the same manner as in Example 1 except that the quantity of the supported ruthenium was changed to 0.5% by weight. It was found that the yield of 1,3-BAC was 3%, that of 1-aminomethyl-3-cyanobenzene 76% and that of metaxylylenediamine 21%.

EXAMPLE 5

10 g of alumina powder containing 5% by weight ruthenium, 22 g of isopthalonitrile, 52 g of dioxane and 30 g of liquid ammonia were charged into an autoclave having a net capacity of 200 cc, provided with an electromagnetic stirrer, and subjected to reaction in the same manner as in Example 1. After the reaction, the liquid in the autoclave was withdrawn by using a nozzle with a filter. Then, 22 g of isopthalonitrile, 52 g of dioxane and 30 g of liquid ammonia were newly charged, and subjected to reaction in the same manner as in Example 1. Thus, the reaction was repeated four times. The yield of 1,3-BAC in each reaction was the first time 87.9%, the second time 88.1%, the third time 87.6% and the fourth time 88.0%. Deterioration of the catalyst activity was not observed.

According to the present invention, BAC can be produced by one step from an aromatic nitrile without using an expensive catalyst, whereby BAC so far produced by two-stage process from the aromatic dinitrile can be obtained with a commercial advantage. Thus, the present invention has an important commercial significance.

What is claimed is:

1. A process for producing bisaminomethylcyclohexane, which consists essentially of hydrogenating an aromatic dinitrile in the presence of a solvent selected from the group consisting of dioxane, tetrahydrofuran and alkylbenzene and a ruthenium catalyst consisting of ruthenium supported on an alumina or activated carbon carrier and containing 1 to 10% by weight of ruthenium, in terms of metallic ruthenium, and in the presence of 0.5 parts by weight or more of liquid ammonia per part by weight of the aromatic dinitrile at a temperature of 70° to 150° C. and a hydrogen partial pressure of 50 to 150 atm.

2. A process for producing bisaminomethylcyclohexane, which consists essentially of hydrogenating an aromatic dinitrile in the presence of a ruthenium catalyst consisting of ruthenium supported on an alumina or activated carbon carrier and containing 1 to 10% by weight of ruthenium, in terms of metallic ruthenium, and in the presence of 0.5 parts by weight or more of liquid ammonia per part by weight of the aromatic dinitrile at a temperature of 70° to 150° C. and a hydrogen partial pressure of 50 to 150 atm and in the absence of a solvent.

* * * * *